United States Patent
Epstein et al.

(10) Patent No.: US 8,359,104 B2
(45) Date of Patent: Jan. 22, 2013

(54) RF COSMETIC REJUVENATION DEVICE AND PROCEDURE

(75) Inventors: Richard Epstein, Buffalo Grove, IL (US); Jonathan Achenbach, New York City, NY (US)

(73) Assignee: Ellman International Inc., Oceanside, NY (US)

( * ) Notice: Subject to any disclaimer, the term of this patent is extended or adjusted under 35 U.S.C. 154(b) by 612 days.

(21) Appl. No.: 12/586,006

(22) Filed: Sep. 17, 2009

(65) Prior Publication Data

US 2011/0066145 A1    Mar. 17, 2011

(51) Int. Cl.
  *A61B 18/18*  (2006.01)
  *A61B 18/14*  (2006.01)
(52) U.S. Cl. .................. 607/101; 606/9; 606/33; 606/41
(58) Field of Classification Search .............. 606/9, 33, 606/41; 607/101
  See application file for complete search history.

(56) References Cited

U.S. PATENT DOCUMENTS

| | | | |
|---|---|---|---|
| 6,409,726 B1 * | 6/2002 | Ellman et al. | 606/45 |
| 6,416,512 B1 * | 7/2002 | Ellman et al. | 606/45 |
| 6,447,509 B1 * | 9/2002 | Bonnet et al. | 606/45 |
| 7,749,218 B2 * | 7/2010 | Pellegrino et al. | 606/41 |
| 2004/0049251 A1 * | 3/2004 | Knowlton | 607/101 |
| 2005/0256524 A1 * | 11/2005 | Long et al. | 606/41 |
| 2007/0093804 A1 * | 4/2007 | Kaveckis et al. | 606/41 |
| 2007/0093805 A1 * | 4/2007 | Auth et al. | 606/41 |
| 2007/0161981 A1 * | 7/2007 | Sanders et al. | 606/41 |
| 2007/0213700 A1 * | 9/2007 | Davison et al. | 606/32 |
| 2007/0282318 A1 * | 12/2007 | Spooner et al. | 606/32 |
| 2008/0058796 A1 * | 3/2008 | O'Brien et al. | 606/40 |

* cited by examiner

*Primary Examiner* — Roy Gibson
*Assistant Examiner* — Kaitlyn Smith
(74) *Attorney, Agent, or Firm* — Ganz Law, P.C.

(57) ABSTRACT

An electrode especially useful for RF skin tightening procedures is characterized by an active front that is conical in part with the conical surface having a cone angle that is shallower than the corresponding angle in known electrodes. Preferably, the electrode of the invention has a conical section whose surface forms an angle greater than 60 degrees with the longitudinal axis of the electrode, and the outside diameter of the conical section is greater than 50% of the overall outside diameter of the electrode.

10 Claims, 5 Drawing Sheets

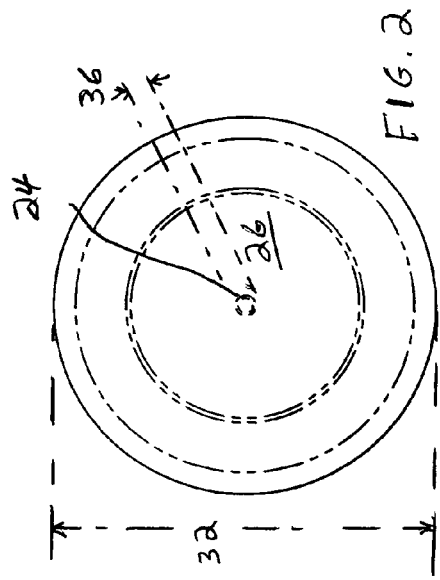
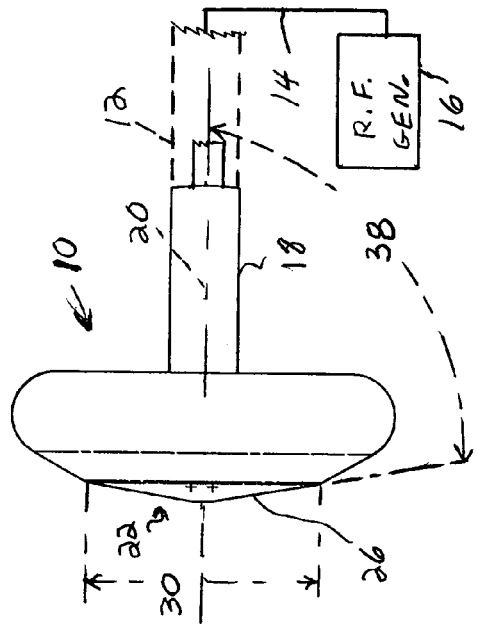
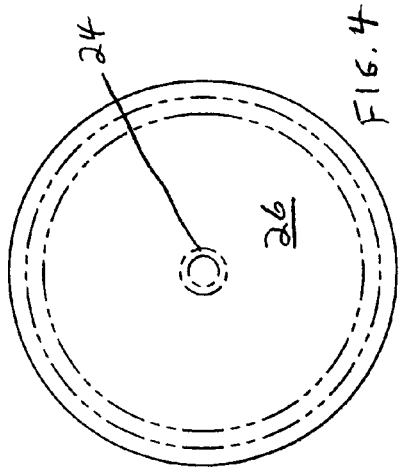
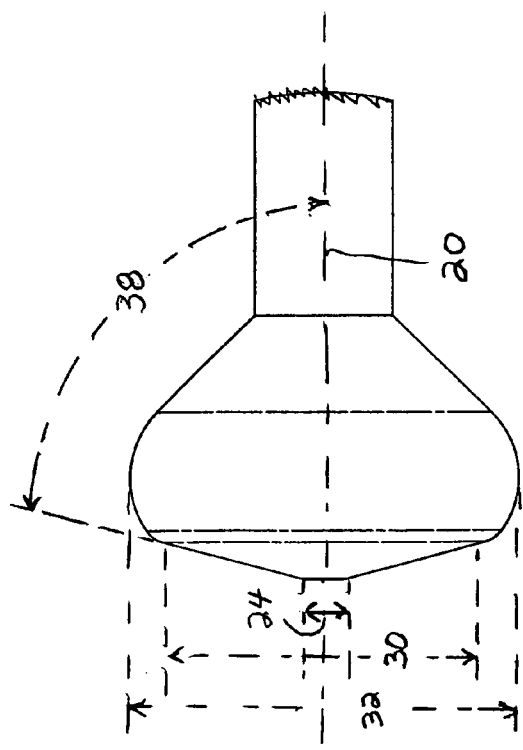

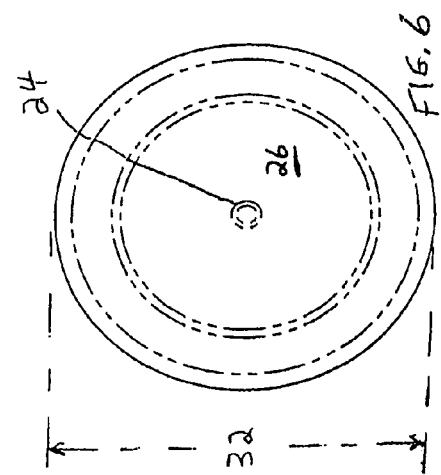
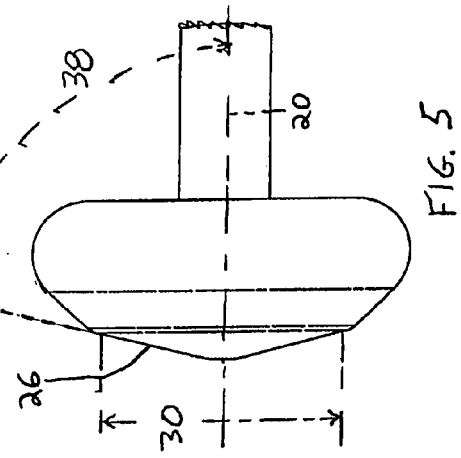
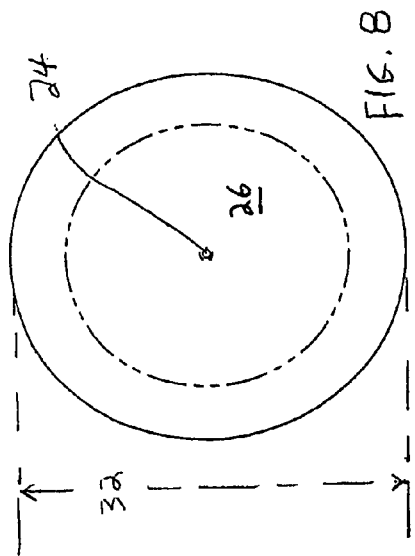
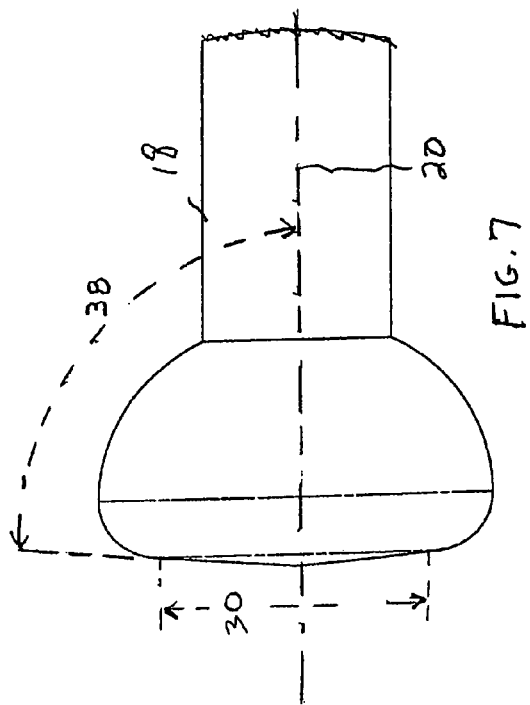

RF COSMETIC REJUVENATION DEVICE AND PROCEDURE

This invention relates to a device and a procedure for cosmetic rejuvenation, and in particular to such device and procedure for treating skin tissue using non-ablative radio-frequency (RF) energy.

BACKGROUND OF THE INVENTION

A commonly-assigned copending application Ser. No. 11/709,672, filed Feb. 23, 2007, the contents of which are herein incorporated by reference, describes an electrode configuration and RF procedure for use for topical application to the tissue surface or skin of a patient for the non-ablative removal of wrinkles or other cosmetic rejuvenation or skin tightening procedures to improve the appearance of skin tissue. In this RF procedure employing RF energy from an RF generator, it is desirable to raise the tissue temperature to about 41-65° C. to affect underlying skin collagen to tighten the surface tissue, being careful to avoid overheating the skin tissue possibly causing burns and residual scarring. As described in this prior application, preferably a dome shaped electrode is employed while pre-applying to the skin a thermal gel, a known thermally and electrically-conductive material, to help cool the surface. The assignee Ellman International, Inc. of Oceanside, N.Y. has also marketed for this purpose under the name RADIAGE an electrosurgical handpiece known as a wand with a built in dome-shaped or ball electrode for use together with a thermal gel to help cool the surface.

SUMMARY OF THE INVENTION

An object of the present invention is to employ RF energy for skin conditioning with an improved non-ablative electrode in a handpiece for supplying RF energy to the electrode while carrying out an improved cosmetic skin-rejuvenation procedure.

A further object of the invention is cosmetic skin-tightening procedure requiring reduced time and generator power settings without the aid of an active cooling mechanism.

These and other objects of the invention are achieved with a novel RF electrode shape with which sufficient RF energy can be applied to a patient's skin to heat skin collagen and tighten the skin without the aid of an active cooling mechanism but still maintain the skin surface at a low enough temperature to avoid burns to the skin surface.

As a further feature of the invention, these results are achieved with a simple lubricating gel that does not provide an endothermic effect to cool, the skin as the gel is free of chondroitin sulfate (or other glycosaminoglcan) or animal protein commonly found in thermal gels.

A preferred electrode embodiment of the invention is characterized by an active front surface that is conical in part with the conical surface having a cone angle that is shallower than the corresponding angle in the known dome-shaped electrode.

Preferably, the electrode of the invention has a conical section whose surface forms an angle greater than 60 degrees with the longitudinal axis of the electrode, and the outside diameter of the conical section is greater than 50% of the overall outside diameter of the electrode. In a further preferred embodiment, the outside diameter of the conical surface is greater than 0.3 inches. Looked at from the front, in accordance with a further feature of the invention, the center of the electrode active surface preferably has a small flat, or curved with greater than 0.025" inside radius, surface leading into the conical section which extends symmetrically rearward from the flat.

The longitudinal axis of the electrode is defined to mean the center line of the electrode head and shank. The front surface of the head, the active surface of the electrode to be placed in contact with the patient's tissue, is symmetrical about the longitudinal axis. The outside diameter measurements are taken in a plane perpendicular to the longitudinal axis. The conical surface preferably terminates at a rounded section whose outside diameter is the overall outside diameter of the electrode.

This novel electrode shape offers several important advantages in a skin tightening procedure. It provides the physician with the ability to apply slightly more intense energy to the tissue being treated by using the small flat or small radiused surface in front and none of or at most a small part only of the surrounding conical surface, whereas by using the flat or radiused surface in front as well as the entire conical surface the physician is provided with the ability to apply a slightly less intense energy to the tissue being treated. This allows the physician to exercise more control over the RF energy density as applied to different skin areas that require less or more RF treatment. In addition, lower power settings can be used for the same results as heretofore and thus it appears that the skin of the patient can be maintained at a lower temperature not requiring the use of active cooling to prevent patient burn. Thus the thermal gel previously recommended can be replaced with a less expensive gel free of the expensive cooling ingredients and that merely acts as a lubricant. A typical gel that can be used contains merely water, a preservative, a thickening agent to stabilize the emulsion, and a hygroscopic agent to aid in wetting the skin.

The various schemes described in the incorporated application disclosures can also be used in the procedure of the present invention, specifically, preferably employing a highly electrically conductive electrode material, and continuously manually moving the activated electrode while in contact with the skin.

Skin tightening employing non-ablative RF is preferred as it is believed that the RF technology produces an electric current that generates heat through resistance in the dermis and subcutaneous skin tissue. The thermal effect depends on the conductivity features of the treated tissue. Collagen fibrils, when heated, will tend to denature and contract, which is believed to lead to the observed tissue tightening. Non-ablative RF treatment has a lower risk of complications, shorter recovery time, and less disruption of regular activities than other skin tightening procedures.

The various features of novelty which characterize the invention are pointed out with particularity in the claims annexed to and forming a part of this disclosure. For a better understanding of the invention, its operating advantages and specific objects attained by its use, reference should be had to the accompanying drawings and descriptive matter in which there are illustrated and described preferred embodiments of the invention, like reference numerals designating the same or similar elements.

BRIEF DESCRIPTION OF THE DRAWINGS

In the drawings:

FIG. 1 is a side schematic view of one form of electrode according to the invention, shown schematically connected to an RF generator of a known type;

FIG. 2 is front view (from the left of FIG. 1) of the electrode of FIG. 1;

FIG. 3 is a side view of another form of electrode according to the invention;

FIG. 4 is a front view (from the left of FIG. 3) of the electrode of FIG. 3;

FIG. 5 is a side view of still another form of electrode according to the invention;

FIG. 6 is a front view (from the left of FIG. 5) of the electrode of FIG. 5;

FIG. 7 is a side view of still another form of electrode according to the invention;

FIG. 8 is a front view (from the left of FIG. 7) of the electrode of FIG. 7;

DETAILED DESCRIPTION OF PREFERRED EMBODIMENTS

Figure 9:
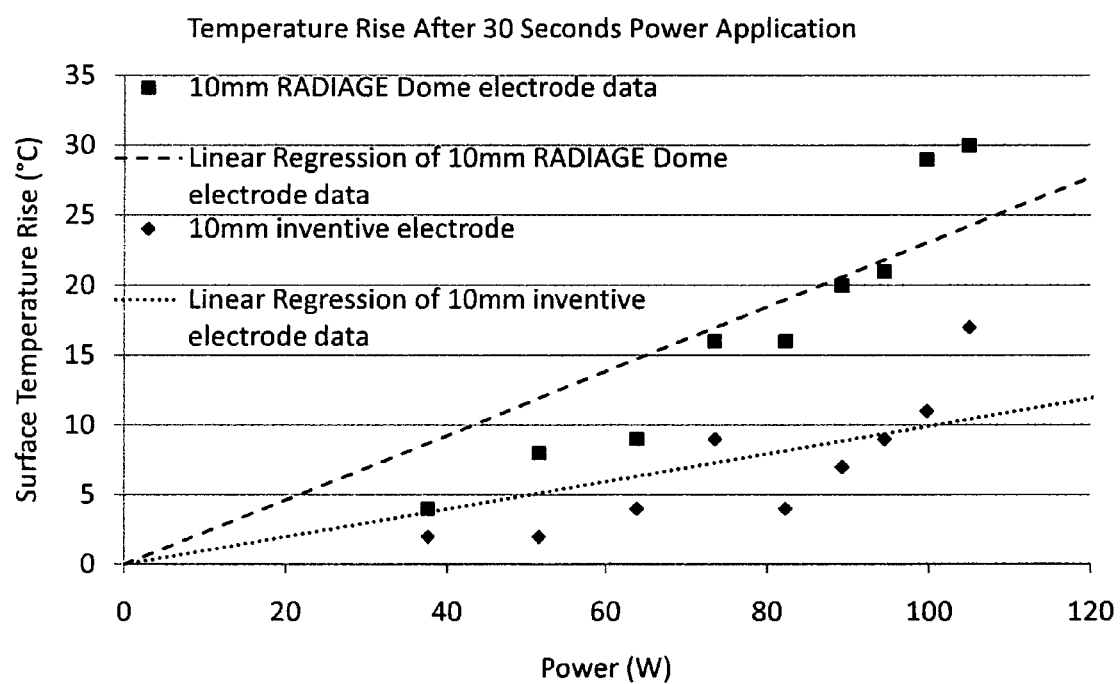
FIG. 9 is a graph plotting surface temperature rise as a function of increasing RF power being applied to a tissue specimen for a 30 second interval.

FIGS. 1 and 2 illustrate a medium size electrode, e.g., 15 mm; FIGS. 3 and 4 illustrate a smaller sized electrode, e.g., 10 mm; FIGS. 5 and 6 illustrate the largest size electrode, e.g., 20 mm; FIGS. 7 and 8 illustrate the smallest sized electrode, e.g., 5 mm, of a family of electrodes used by a physician in RF skin tightening procedures. At least the outer surface of all electrodes are electrically-conductive for a thickness of at least the skin depth of the operating frequency, preferably made of a highly conductive metal, though the electrode can be made wholly of the metal. The electrode is referred to in the claims as a body 10.

FIGS. 1 and 2 illustrate a medium sized electrode 10, e.g., 15 mm diameter. It is shown mounted in a handpiece 12 (shown schematically in dashed lines), and connected via a standard cable 14 to a conventional RF generator 16. The electrode 10 and its shank 18 have a common longitudinal axis 20. The active surface of the electrode is the front-facing surface 22 which is electrically conductive as described above and which is symmetrical about the longitudinal axis 20. The active surface 22 comprises a small flat 24 at the center surrounded by a conical surface 26. The largest or outside diameter of the conical surface (referred to in the claims as the "first outside diameter") is designated 30 and for the embodiment shown is about 0.388 inches, the largest or outside diameter of the electrode, i.e., the overall diameter measured in a plane perpendicular to the longitudinal axis, (referred to in the claims as the "second outside diameter") is designated 32 and for the embodiment shown is about 0.59. Thus, the largest cone diameter 30 is about 66% of the largest electrode diameter 32. The diameter of the small flat 24 at the front (FIG. 2) is designated 36, and for the embodiment shown is about 0.031 inches. The center flat 24 lies in a plane perpendicular to the longitudinal axis, and the lateral surface of the conical surface 26 forms a shallow angle designated 38 with the longitudinal axis 20 for the embodiment shown of about 75°.

The corresponding dimensions of the electrode shown in FIGS. 3 and 4, for the 10 mm diameter electrode, are as follows (the same reference numerals are used for corresponding electrode parts): the largest diameter 30 of the conical surface is about 0.33 inches; the largest diameter 32 of the electrode is about 0.39; the largest cone diameter 30 is about 83% of the largest electrode diameter 32. The diameter of the small flat 24 at the front is designated 36, and for the embodiment shown is about 0.031 inches. The conical surface 26 forms a shallow angle designated 38 with the longitudinal axis 20 of about 75° (FIG. 3).

The corresponding dimensions of the electrode shown in FIGS. 5 and 6, for the 20 mm diameter electrode, are as follows (the same reference numerals are used for corresponding electrode parts): the largest diameter 30 of the conical surface 26 is about 0.47 inches; the largest diameter 32 of the electrode is about 0.78; the largest cone diameter 30 is about 60% of the largest electrode diameter 32. The diameter of the small flat 24 at the front is designated 36 (corresponding to 36 in FIG. 2), and for the embodiment shown is about 0.031 inches. The conical surface 26 forms a shallow angle designated 38 with the longitudinal axis (20) of about 80°.

For these three electrode dimensions, the 10, 15 and 20 mm, the diameter 36 of the small flat 24 is less than 10% of the diameter 30 of the largest diameter of the conical section 26. The values are 9.5, 8.0, and 6.6% of the conical diameter, respectively. Preferably, for electrodes equal to or greater than 8 mm, it is preferred that the diameter 36 of the small flat 24 (FIG. 2) is between 5 and 10% of the diameter 30 (FIG. 3) of the largest diameter of the conical section 26, so that enough of the center flat 24 is available for more intense heating, while maintaining most of the available active surface conically shaped for less intense heating which is the more common procedure.

The small front center section 24, instead of flat, can also be a small curved (concave) surface with an inside radius exceeding 0.025 inches. So, as with the flat section, when used alone, more intense heating but not over-heating is achieved. Preferably, the small front center section 24 if curved has a surface area that is less than 10% of the surface area of the conical surface 26. Preferably, when the overall diameter 32 of the electrode is greater than 8 mm, and the small surface section 24 in front is curved, it has a diameter that is between 5 and 10% of the widest part 30 of the conical surface 26.

The corresponding dimensions of the electrode shown in FIGS. 7 and 8, for the 5 mm diameter electrode, are as follows (the same reference numerals are used for corresponding electrode parts): the largest diameter 30 of the conical surface 26 is about 0.14 inches; the largest diameter 32 of the electrode is about 0.2 inches; the largest cone diameter 30 is about 70% of the largest electrode diameter 32. Since the dimensions of the 5 mm electrode are so small, the diameter of the center flat 24 in front approaches zero, and virtually blends in to the conical section. The conical surface 26 forms a shallow angle designated 38 with the longitudinal axis 20 of about 85°.

The important features are that the active surface 22 of the electrode comprises the shallow angled conical surface 26 which cooperates with the small flat or small radiussed curved surface 24 in front center such that the physician can control more accurately the RF energy density at the tissue surface. By the physician positioning the active electrode surface such that only the small flat or curved center front section 24 is in contact with the skin, the RF energy density can be maximized for the same power settings because the RF currents exit only via the small surface area of the front section 24. On the other hand, when the physician positions the active electrode surface such that not only the flat or curved front section 24 but also the conical section 26 is in contact with the skin, the RF energy density can be minimized for the same power settings because the RF currents exit now via a much larger surface area of the combined flat or curved and conical sections 24, 26. This takes advantage of the resilience of the skin tissue that allows the contacted electrode surface area to be controlled due to the shallow cone angle present.

It has also been found that the new geometry described herein also offers the advantage of maintaining the skin surface at lower temperatures thus avoiding the use of active cooling means to prevent burns. An ordinary lubricating gel lacking any special cooling ingredients can be used to lower costs.

Tests have been conducted comparing the heating effect on tissue of a 10 mm RADIAGE dome electrode and the electrode in accordance with the invention. The RADIAGE dome electrode is an electrode currently sold by Ellman International, Inc. of Oceanside, N.Y. for purposes of cosmetic rejuvenation. Its dimensions are as follows: The dome electrode's outside diameter is 0.39 inches. It has an inner 0.29 inch diameter region where the dome has a 0.27 inch radius. The region between the diameters of 0.29 inch and 0.39 inch is a surface with a 0.10 inch radius which continues to the backside of the electrode. The 0.27 inch and 0.10 inch radiuses are blended together at their transition.

The tests were conducted on a piece of beef using the 10 mm RADIAGE dome electrode described above and a 10 mm electrode as described herein in accordance with the invention with the new non-cooling gel for both electrodes. The surface temperature was measured with an IR sensor immediately before and after applying RF energy from a standard RF generator at 4.0 MHz, in this instance made by Ellman International, Inc. of Oceanside, N.Y.

Figure 10:
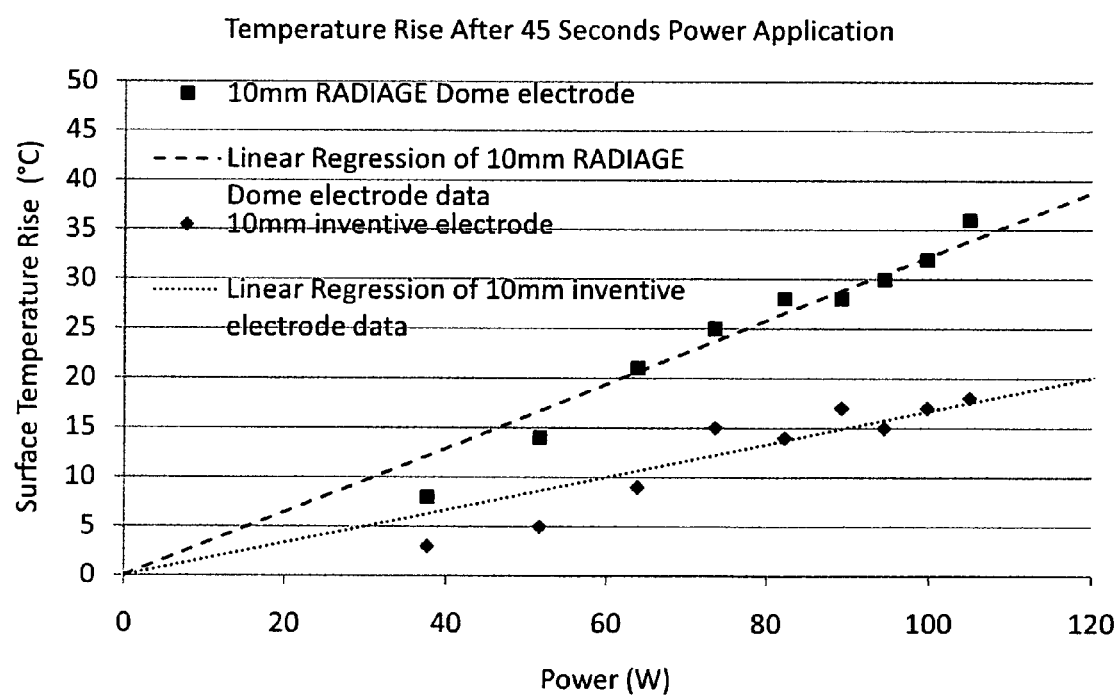
FIG. 10 is a graph plotting surface temperature rise as a function of increasing RF power being applied to a tissue specimen for a 45 second interval.
Figure 11:
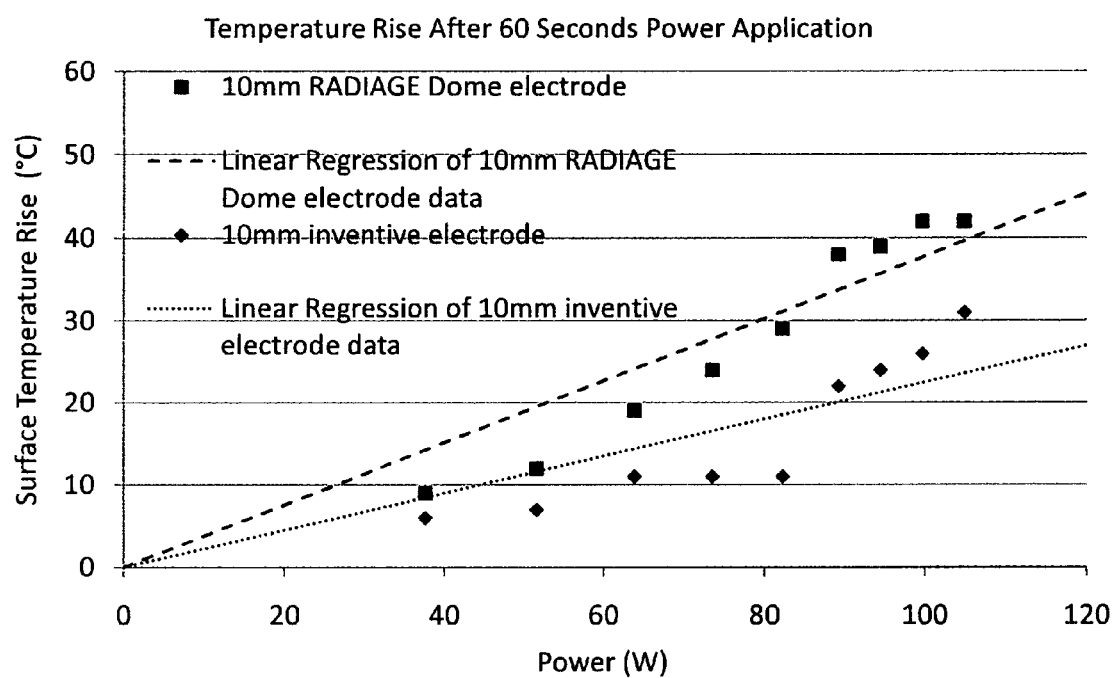
FIG. 11 is a graph plotting surface temperature rise as a function of increasing RF power being applied to a tissue specimen for a 60 second interval.

The graphs of FIGS. 9-11 show the results; plots of the temperature rise of the specimen measured with increasing power applied for 30, 45, and 60 seconds. In the graphs, the diamond points represent measurements taken with the known RADIAGE dome electrode with the dashed line representing the linear least squared regression of those data points with zero intercept, whereas the square points represent measurements taken with the electrode in accordance with the invention with the dotted line representing the linear least squared regression of those data points with zero intercept. The slopes of the regressions for the known dome electrode are 0.23, 0.32, and 0.38 for the temperature rise after 30, 45, and 60 seconds. The slopes of the regressions for the 10 mm inventive electrode are 0.10, 0.17, 0.22, for the temperature rise after 30, 45, and 60 seconds. As will be noted, the electrode in accordance with the invention produces significantly less surface temperature elevation supporting the reduced need for active surface cooling.

The RF generator used preferably output RF currents in the range of about 0.2-10 MHz. Continuous wave power can be used.

While the invention has been described in connection with preferred embodiments, it will be understood that modifications thereof within the principles outlined above will be evident to those skilled in the art and thus the invention is not limited to the preferred embodiments but is intended to encompass such modifications.

What is claimed is:

1. A device for use in a surgical procedure for improving the appearance of skin tissue of a patient by applying RF energy thereto, the device comprising:
   (a) a handpiece having means for receiving RF energy from a generator when activated, the handpiece supporting an electrode having an active surface in front to be brought into contact with the patient's skin to apply the received RF energy to the skin when the generator is activated, characterized in that:
   the electrode comprises:
   (b) a body (10) with an electrically-conductive surface having a longitudinal axis (20) in which the active surface (22) in front comprises a conical surface (26) symmetrically aligned with the longitudinal axis and widening rearward from the front, the conical surface (26) having an axis aligned with the longitudinal axis with the conical surface (26) forming an angle (38) with the longitudinal axis (20) that exceeds 60°.

2. A device as set forth in claim 1, wherein:
   (c) the largest part of the conical surface (26) measured in a plane perpendicular to the longitudinal axis (20) has a first outside diameter (30) exceeding 0.3 inches.

3. A device as set forth in claim 1, wherein:
   (d) the body (10) has a largest part with a second outside diameter (32) measured in a plane perpendicular to the longitudinal axis (20),
   (e) the first outside diameter (30) being greater than 50% but less than 100% of the second outside diameter (32).

4. A device for use in a surgical procedure for improving the appearance of skin tissue of a patient by applying RF energy thereto, the device comprising:
   (a) a handpiece having means for receiving RF energy from a generator when activated, the handpiece supporting an electrode having an active surface in front to be brought into contact with the patient's skin to apply the received RF energy to the skin when the generator is activated, characterized in that:
   the electrode comprises:
   (b) a body (10) with an electrically-conductive surface having a longitudinal axis (20) in which the active surface (22) in front comprises aligned with the longitudinal axis a small flat, or curved with greater than 0.025" radius, surface (24) leading into a conical surface (26) symmetrically aligned with the longitudinal axis (20) and widening rearward from the front, the conical surface (26) having an axis aligned with the longitudinal axis (20) with the conical surface (26) forming an angle (38) with the longitudinal axis that exceeds 60°.

5. A device as set forth in claim 4, wherein:
   (c) the largest part of the conical surface measured in a plane perpendicular to the longitudinal axis having a first outside diameter (30) exceeding 0.3 inches.

6. A device as set forth in claim 4, wherein:
   (d) the body having a largest part with a second outside diameter (32) measured in a plane perpendicular to the longitudinal axis,
   (e) the first outside diameter (30) being greater than 50% but less than 100% of the second outside diameter (32).

7. A device as claimed in claim 4, wherein the small flat, or curved with greater than 0.025" radius, surface (24) of the active surface (22) in front is flat having a diameter that is less than 10% of the surface area of the conical surface (26).

8. A device as claimed in claim 4, wherein the overall second outside diameter (32) of the electrode is greater than 8 mm, and the small flat, or curved with greater than 0.025" radius, surface (24) of the active surface (22) in front is flat having a diameter that is between 5 and 10% of the largest part of the conical surface (26).

9. A device as claimed in claim 4, wherein the small flat, or curved with greater than 0.025" radius, surface (24) of the active surface (22) in front is curved having a surface area that is less than 10% of the surface area of the conical surface (26).

10. A device as claimed in claim 4, wherein the overall second outside diameter (32) of the electrode is greater than 8 mm, and the small flat, or curved with greater than 0.025" radius, surface (24) of the active surface (22) in front is curved having a diameter that is between 5 and 10% of the largest part of the conical surface.

* * * * *